United States Patent
Dallavalle et al.

(10) Patent No.: US 7,351,714 B2
(45) Date of Patent: *Apr. 1, 2008

(54) 7-IMINO DERIVATIVES OF CAMPTOTHECIN HAVING ANTITUMOR ACTIVITY

(75) Inventors: Sabrina Dallavalle, Vimercate (IT); Sergio Penco, Milan (IT); Claudio Pisano, Pomezia (IT); Franco Zunino, Milan (IT)

(73) Assignees: Sigma-Tau Industrie Farmaceutiche Riunite S.p.A., Rome (IT); Istituto Nazionale per Lo Studio E La Cura Dei Tumori, Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 10/546,211

(22) PCT Filed: Mar. 10, 2004

(86) PCT No.: PCT/IT2004/000118

§ 371 (c)(1),
(2), (4) Date: Feb. 6, 2006

(87) PCT Pub. No.: WO2004/083214

PCT Pub. Date: Sep. 30, 2004

(65) Prior Publication Data

US 2006/0167033 A1    Jul. 27, 2006

(51) Int. Cl.
*A61K 31/4745* (2006.01)
*C07D 491/22* (2006.01)

(52) U.S. Cl. ........................... 514/283; 546/48
(58) Field of Classification Search ................ 514/283; 546/48
See application file for complete search history.

(56) References Cited

U.S. PATENT DOCUMENTS 6,242,457 B1 * 6/2001 Penco et al. ................ 514/283
6,589,939 B2 * 7/2003 Penco et al. .................. 514/25
7,105,492 B2 * 9/2006 Dallavalle et al. ............ 514/25

FOREIGN PATENT DOCUMENTS

EP    0 056 692    7/1982
EP    0 088 642    9/1983
EP    1 044 977    10/2000
WO    97/31003    8/1997

OTHER PUBLICATIONS

International Search Report for PCT/IT2004/000118 dated Jul. 14, 2004.
Dallavalle et al., *Novel Cytotoxic 7-Iminomethyl and 7-Aminomethyl Derivatives of Camptothecin*, Bioorganic & Medicinal Chemistry Letters, 11(3), 291-294, XP-002286415.
Sinha, *Topoisomerase Inhibitors*, Drugs, vol. 49, No. 1, 1995, pp. 11-19, XP-002116367.
Wang et al., *Synthesis of Novel Water-Soluble 7-(Aminoacylhydrazono)-formyl Camptothecins with Potent Inhibition of DNA Topoisomerase 1*, Bioorganic & Medicinal Chemistry, vol. 2, No. 12, 1994, pp. 1397-1402, XP-002116366.
Sawada et al., *Chemical Modification of an Antitumor Alkaloid Camptothecin: Synthesis and Antitumor Activity of 7-C-Substituted Camptothecins*, Chemical and Pharmaceutical Bulletin, vol. 39, No. 10, Oct. 1, 1991, pp. 2574-2580, XP-002034620.

* cited by examiner

*Primary Examiner*—Charanjit S. Aulakh
(74) *Attorney, Agent, or Firm*—Nixon & Vanderhye P.C.

(57) ABSTRACT

Camptothecin derivatives of camptothecin of formula (I)

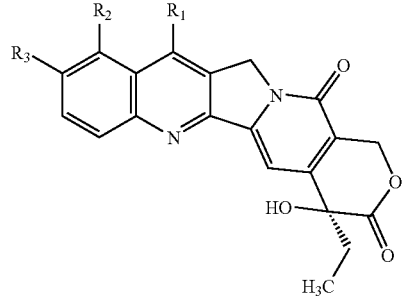

wherein the groups $R_1$, $R_2$ and $R_3$ are as defined in the description are disclosed.

The compounds of formula (I) are endowed with antitumor activity and show a good therapeutic index.

Processes for the preparation of the compounds of formula (I) and their use in the preparation of medicaments useful in the treatment of tumors, viral infections and antiplasmodium *falciparum* are also disclosed.

3 Claims, No Drawings

7-IMINO DERIVATIVES OF CAMPTOTHECIN HAVING ANTITUMOR ACTIVITY

This application is the U.S. national phase of international application PCT/IT2004/000118 filed 10 Mar. 2004 which designated the U.S. and claims benefit of U.S. Ser. No. 10/388,587, filed 17 Mar. 2003, the entire contents of each of which are hereby incorporated by reference.

The present invention relates to compounds having antitumor activity, in particular to new derivatives of camptothecins, processes for their preparation, their use as antitumor drugs and pharmaceutical compositions containing them as active ingredients.

BACKGROUND OF THE INVENTION

Camptothecin is an alkaloid, which was isolated by Wall et al. (*J. Am. Chem. Soc.* 88, 3888-3890 (1966)) for the first time from the tree *Camptoteca acuminata*, a plant originating from China, of the Nyssaceae family.

The molecule consists of a pentacyclic structure having a lactone in the ring E, which is essential for cytotoxicity.

The drug demonstrated a wide spectrum of antitumor activity, in particular against colon tumors, other solid tumors and leukemias, and the first clinical trials were performed in the early 70's. Since Camptothecin (in the following briefly CPT) has low water solubility and in order to prepare clinical trials, the National Cancer Institute (NCI) prepared the sodium salt (NSC100880), which is water-soluble. Clinical trials in phase I and II, were not completed because of the high toxicity showed by the compound (hemorrhagic cystitis, gastrointestinal toxicity, such as nausea, vomit, diarrhoea, and myelosuppression, especially leucopenia and thrombocytopenia.

In any case, sodium salt showed a lower activity than CPT, because, at pH 7.4, the inactive form (open ring) predominates on the lactone-active one (closed ring), which predominates at pH<4.0.

Subsequently, many CPT analogues were synthesised in order to obtain compounds with lower toxicity and higher water solubility. Two drugs are marketed, Irinotecan (CPT-11), marketed with the Trade Mark Camptosar® by Upjohn and Topotecan, marketed with the Trade Mark Hymcamptamin® or Thycantin®, by Smith Kline & Beecham. Other derivatives are in different steps of clinical development in phase II, such as NSC-603071 (9-amino-camptothecin), 9-NC or 9-nitrocamptothecin, an oral prodrug converted in 9-aminocamptothecin, GG-211 (GI 147211), and DX-8591f, the latter being water-soluble. All the derivatives identified to-date contain the parent structure with 5 rings, essential for cytotoxicity. It was demonstrated that modifications on the first ring, such as in the case of the above-mentioned drugs increase water solubility and allow a higher tolerability of the drug.

Water-soluble Irinotecan was approved for the treatment of many solid tumors and ascites (colon-rectum, skin, stomach, breast, small and non-small cell lung, cervix and ovarian cancer and in non-Hodgkin lymphoma). Moreover, Irinotecan resulted active in solid tumors resistant to Topotecan, vincristine or melphalan and MDR-1 cells resulted marginally resistant to the drug. The active metabolite was identified as the 10-hydroxyderivative (SN-38), produced by the action of carboxylesterases. CPT-11 showed a good activity using different administration routes, such as intraperitoneal, intravenous, oral (Costin, D., Potinhexyl, M. *Advances in Pharmacol.*, 29B, 51-72 1994).

CPT-11 was administered also with cisplatin or etoposide, showing a synergistic effect, thanks to the ability to hinder DNA repair. Also in this case, however, a grade 3 and 4 leucopenia and diarrhoea arose (Sinha, B. K., (1995), *Topoisomerase inhibitors. Drugs,* 49, 11-19, 1995).

Topotecan has a significant oral bioavailability. Oral administration proved to be convenient to reach a prolonged exposition to the drug, without the use of temporary catheters being necessary (Rothenberg, M. L., *Annals of Oncology,* 8, 837-855, 1997). Also this water-soluble CPT analogue showed activity against different types of tumors, with different administration routes, intraperitoneal, intravenous, subcutaneous, oral The more promising results were obtained with Topotecan hydrochloride, intravenous infusion for 5 days, in different tumors such as small and non-small cell lung, ovarian, breast, stomach, liver, prostate, soft tissue sarcoma, head and neck, oesophagus, resistant colon-rectum, multiform glioblastoma, chronic and acute myelocytic leukemias. However, also in this case, severe side effects occurred, such as neutropenia and thrombocytopenia, whereas gastrointestinal toxicity, such as nausea, vomit and diarrhoea were milder.

It was demonstrated that the main transformation and elimination pathways of the drug comprise lactone hydrolysis and urinary excretion: in fact, lactone form is 50% hydrolysed to open ring, 30 minutes after infusion. Topotecan crosses hematoencephalic barrier 10 minutes after infusion (30% in the cerebrospinal fluid with respect to plasma). On the contrary, camptothecin does not cross hematoencephalic barrier in significant amount, probably due to its binding with proteins.

Clinical development of 9-aminocamptothecin was hampered by its scarce water solubility. Recently, a colloidal dispersion was prepared, which made possible its entry in phase II clinical trial. Prolonged exposition (from 72 hours to 21 days) appeared to be essential to demonstrate antitumor activity, because of its short half-life (Dahut, et al., 1994). Responses in patients suffering from not treated colon-rectum, and breast cancer and resistant lymphoma, were noticed. The activity demonstrated against Pgp-positive tumors suggested a lack of cross-resistance against resistant MDR-1 cells. Once again, bone marrow and gastrointestinal toxicity was observed.

Lurtotecan is the most water-soluble analogue, with an activity comparable to Topotecan in vitro. Two regimens were adopted: one 30-minutes infusion a day for 5 days every 3 weeks and one 72-hours infusion one time every 3 weeks. Responses in patients suffering from, neck, ovarian, breast, liver tumour were observed. Also in this case, haematic toxicity was detected.

The molecule is the following:

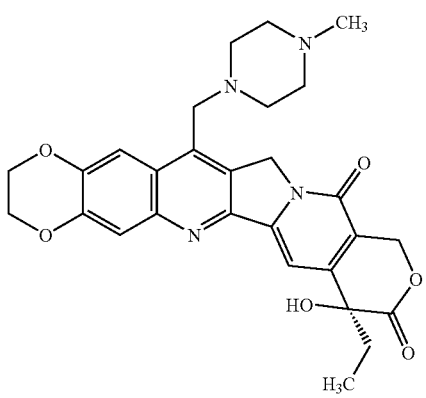

9-Nitrocamptothecin is an oral prodrug rapidly converted into 9-aminocamptothecin after administration. Responses were observed in patients suffering from pancreas, ovarian, and breast cancer.

Notwithstanding the major part of tumour cells is highly sensitive to topoisomerase I inhibitors, due to the high enzyme levels, some tumoral lines result to be resistant. This is due to other mechanisms, rather than the overexpression of MDR1 and MRP (multidrug resistance associated protein) genes and of their products, P (Pgp) glycoprotein and MRP protein, respectively, for which Topotecan or CPT-11 are not very good substrates, (Kawato, Y, et al., *J. Pharm. Pharmacol.*, 45, 444-448, (1993)).

In fact, it was observed that some resistant tumour cells contain mutant forms of topo I, accordingly the formation of the topo I-DNA complex is damaged or some cells lack in the carboxylesterase activity, necessary for converting CPT-11 in the active metabolite SN-38 and are thus resistant against this drug (Rothenberg, 1997, ibid.).

Within the drugs used in tumour therapy, the interest in inhibitors of topoisomerase I enzymes is attributed to the following considerations: a) efficacy against tumors naturally resistant to conventional drugs, topoisomerase II inhibitors included; b) the levels of the topo I enzyme remain elevated in all phases of the cycle; c) many tumors express high levels of the target enzyme; d) lack of recognition by the proteins involved in the phenomenon of multi-drug resistance (Pgp or MRP) and absence of the detoxifying enzyme-mediated metabolism, associated to the glutathione-dependent system (glutathione peroxidase and glutathione S-transferase) (Gerrits, C J H., et al., *Brit. J. Cancer*, 76, 952-962).

Once potential clinical advantages of topoisomerase I inhibitors are taken into consideration, both in terms of antitumor activity, assayed on a wide range of tumors, and the poor induction of pharmaco-resistance, the present research aims to identify topo I inhibitors with a lower toxicity with respect to the one demonstrated by the drugs on the market or in clinical phase. The factors determining the relative potency of camptothecin analogues include a) intrinsic activity of topoisomerase I inhibition; b) drug mean life; c) interaction with plasma proteins; d) the ratio between the circulating active form (lactone) and the non active one (carboxylate); e) drug sensitivity relative to cell outflow mediated by glycoprotein P or MRP; f) bond stability with topoisomerase I (Rothenberg, 1997, ibid.).

Among the main adverse effects of Irinotecan and other camptothecins derivatives, myelosuppression and gastrointestinal toxicity, such as diarrhoea and vomit, have been observed. Diarrhoea can have an early or late onset and can be a dose-limiting factor. Vomit and late diarrhoea are induced by many antitumor drugs, while early diarrhoea occurring during or immediately after infusion is almost specific for Irinotecan and some camptothecin derivatives.

Toxic effects occur mainly in the intestinal tract.

In order to reduce diarrhoea, CPT-11 was administered in some clinical trials, in combination with loperamide, a synthetic oppioid, agonist of the mu-oppioid enteric receptors (*Abigerges*, 1994; *Abigerges*, 1995), as well as with an inhibitor of the enkephalinases (acetorfan) or with ondansetron, an antagonist of the 5-HT$_3$ receptors, or with diphenidramine, an antagonist of H$_1$ receptors.

To date, the problems connected with the use of camptothecin derivatives as antitumor drugs can be summarised in the following items:

camptothecin (CPT), and many of its active derivatives have low water solubility;

the subsequent derivatives are endowed with severe side effects at gastrointestinal and bone marrow level;

some tumour lines developed resistance against topoisomerase I inhibitors;

there is the constant search for a better therapeutic index.

Patent application WO 97/31003 discloses derivatives of camptothecins substituted at positions 7, 9 and 10. Position 7 provides the following substitutions: —CN, —CH(CN)—R$_4$, —CH=C(CN)—R$_4$, —CH$_2$—CH=C(CN)—R$_4$, —C(=NOH)—NH$_2$, —CH=C(NO$_2$)—R$_4$, —CH(CN)—R$_5$, —CH(CH$_2$NO$_2$)—R$_5$, 5-tetrazolyl, 2-(4,5-dihydroxazolyl), 1,2,4-oxadiazolidin-3-yl-5-one, wherein R$_4$ is hydrogen, linear or branched alkyl from 1 to 6 carbon atoms, nitrile, carboxyalkoxy. Of these possible compounds, WO 97/31003 enables the disclosure only of camptothecin derivatives bearing at position 7 the group —CN and —CH=C(CN)$_2$, with unsubstituted positions 9 and 10.

Of these compounds, the best one proved to be the 7-nitrile (R$_4$=—CN), hereinafter named CPT 83, with cytotoxic activity on non-small cells lung carcinoma (non-SCLC, H-460). This tumour line is intrinsically resistant to cytotoxic therapy and is only moderately responsive to topoisomerase I inhibitors, notwithstanding the overexpression of the target enzyme. CPT 83 is more active than Topotecan, taken as reference compound and on the whole it offers a better pharmacological profile, even in terms of tolerability, then a better therapeutic index.

CPT 83 is prepared through a synthesis route comprising the oxidation of 7-hydroxymethylcamptothecin to camptothecin 7-aldehyde, the transformation of the latter into oxime and final conversion into nitrile.

The starting compound and the intermediates are disclosed in Sawada et al., *Chem. Pharm. Bull.*, 39, (10), 2574, (1991). This paper makes reference to a patent family with priority of 1981, for example European patent application EP 0 056 692, published in 1982. In these publications there are disclosed, among others, the compounds camptothecin 7-aldehyde and its oxime. The usefulness of these derivatives is to provide compounds with antitumor activity having low toxicity starting from 7-hydroxymethylcamptothecin. In the paper published on *Chem. Pharm. Bull.*, 39, (10) 2574, (1991), the authors demonstrate that, with respect to camptothecin, the 7-alkyl and 7-acyloxymethyl derivatives, which were not foreseen in the above mentioned patent application, are the more active compounds on lines of murine leukemia L1210, while lower activity, always with respect to camptothecin, was observed in compounds bearing 7-substitutions with high polar character, such as hydrazones and the oxime —CH(=NOH).

EP 1 044 977 discloses camptothecin derivatives bearing an oxime O-substituted at position 7. The general formula comprises also camptothecin derivatives bearing an enamine group at position 7. In this reference, the main teaching is directed to the antitumor activity of oxime derivatives, while imines are given in only few examples of synthetic preparation, but no pharmacological data are provided. Subsequent work of the inventors of the above mentione patent was focused on oxime derivatives, in particular the tert-butoxy one, which, under the name of Gimatecan is now under clinical trial. Imines were considered just an alternative to oximes, but first pharmacological assays discouraged further development of this class.

ABSTRACT OF THE INVENTION

It has now surprisingly been found that camptothecins bearing an aromatic enamino group on position 7 are endowed with antitumor activity. Said compounds have better therapeutic index.

Accordingly, it is an object of the present invention compounds of general formula (I):

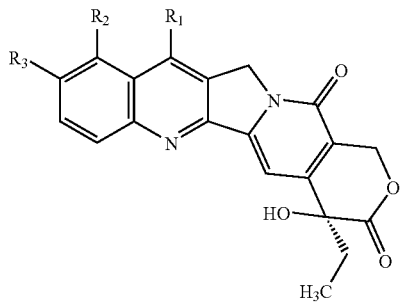

wherein: $R_1$ is a —$C(R_5)$=N—$R_4$ group, wherein $R_4$ is a phenyl group, optionally substituted with one or more groups selected from the group consisting of: halogen, hydroxy, keto, $C_1$-$C_8$ alkyl, $C_1$-$C_8$ alkoxy, phenyl, cyano, nitro, —$NR_6R_7$, wherein $R_6$ and $R_7$, the same or different between them, are hydrogen, ($C_1$-$C_8$) linear or branched alkyl; —S—S-(2-aminophenyl), —S—S-(4-aminophenyl), —S-(4-aminophenyl), —$SCH_3$ and —$CH_2ON$=$C(CH_3)_2$;

$R_5$ is hydrogen, $C_1$-$C_8$ linear or branched alkyl, $C_1$-$C_8$ linear or branched alkenyl, $C_3$-$C_{10}$ cycloalkyl, ($C_3$-$C_{10}$) cycloalkyl-($C_1$-$C_8$) linear or branched alkyl, $C_6$-$C_{14}$ aryl, ($C_6$-$C_{14}$) aryl-($C_1$-$C_8$) linear or branched alkyl;

$R_2$ and $R_3$, the same or different between them are hydrogen, hydroxy, $C_1$-$C_8$ linear or branched alkoxy;

their $N_1$-oxides, their single isomers, in particular the syn and anti isomers of the —$C(R_5)$=N—$R_4$ group, their possible enantiomers, diastereoisomers and relative admixtures, the pharmaceutically acceptable salts thereof and their active metabolites.

The present invention comprises the use of the compounds of the above-mentioned formula (I) as active ingredients for medicaments, in particular for medicaments useful for the treatment of tumors. A further object of the present invention is also the use of the compounds of formula (I) as active ingredients for medicaments useful for treating viral infections. Another object of the present invention is also the use of the compounds of formula (I) as active ingredients for medicaments having antiplasmodium *falciparum* activity.

The present invention comprises pharmaceutical compositions containing compounds of formula (I) as active ingredients, in admixture with pharmaceutically acceptable vehicles and excipients.

The present invention comprises also processes for the preparation of compounds of formula (I), and the relative key intermediates.

DETAILED DESCRIPTION OF THE INVENTION

Within the scope of the present invention, as examples of $C_1$-$C_8$ linear or branched alkyl group, methyl, ethyl, propyl, butyl, pentyl, octyl are meant and their possible isomers, such as for example isopropyl, isobutyl, tert-butyl.

As halogen it is intended fluorine, chlorine, bromine, iodine.

Examples of pharmaceutically acceptable salts are, in case of nitrogen atoms having basic character, the salts with pharmaceutically acceptable acids, both inorganic and organic, such as for example, hydrochloric acid, sulfuric acid, acetic acid, or, in the case of acid group, such as carboxyl, the salts with pharmaceutically acceptable bases, both inorganic and organic, such as for example, alkaline and alkaline-earth hydroxides, ammonium hydroxide, amine, also heterocyclic ones.

A first group of preferred compounds is the one wherein $R_4$ is phenyl substituted by at least one a residue selected from the group consisting of: methyl, ter-butyl, methoxy, hydroxy, chloro, iodio, nitro, —S—S-(2-aminophenyl), S—S-(4-aminophenyl), —S-(4-aminophenyl), —$SCH_3$ and —$CH_2ON$=$C(CH_3)_2$. In particular, the phenyl group is most preferably substituted in ortho-position.

A second group of particularly preferred compounds comprises:

7-(2-methylphenyl)iminomethylcamptothecin (ST2212)

7-(2-chlorophenyl)iminomethylcamptothecin (ST2228)

7-(2,6-dimethylphenyl)iminomethylcamptothecin (ST2317)

7-(2-iodophenyl)iminomethylcamptothecin (ST2316)

7-(2-methoxyphenyl)iminomethylcamptothecin (ST2343)

7-(4-methylphenyl)iminomethylcamptothecin (ST2478)

7-(2-hydroxyphenyl)iminomethylcamptothecin (ST2389)

7-(4-chlorophenyl)iminomethylcamptothecin (ST2412)

7-(4-methoxyphenyl)iminomethylcamptothecin (ST2477)

7-[(4-isopropylidene-amino-oxymethyl)phenyl]iminomethylcamptothecin (ST2460)

7-(2-t-butylphenyl)iminomethylcamptothecin (ST2388)

7-phenyliminomethylcamptothecin (ST1546)

7-(4-nitrophenyl)iminomethylcamptothecin (ST1561)

7-2-(2-aminophenyldithio)phenyliminomethylcamptothecin (ST1737)

7-4-(4-aminophenyldithio)phenyliminomethylcamptothecin (ST2034)

7-4-(4-aminophenylthio)phenyliminomethylcamptothecin (ST2069)

7-(2-methylthiophenyl)iminomethylcamptothecin (ST2138)

7-(4-tert-butylphenyliminomethyl)-camptothecin (ST2619)

7-(4-methylthiophenyliminomethyl)-camptothecin (ST2667)

7-(4-hydroxyphenyliminomethyl)-camptothecin (ST2616)

The compounds of formula (I) can be prepared with different methods according to the nature of the $R_4$ group linked to the nitrogen of the 7-iminomethyl group.

The compounds of formula (I) wherein $R_4$ is as above defined can be prepared starting from camptothecin 7-aldehyde (formula Ia, $R_5$ hydrogen) or 7-keto camptothecin (formula Ia, $R_5$ different from hydrogen),

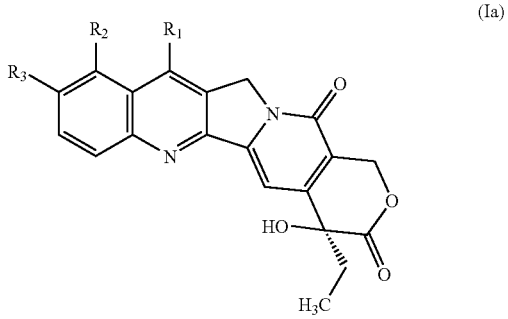

(Ia)

wherein R$_1$ is the group —C(R$_5$)=O, and R$_5$ is as defined for the formula (I), R$_2$ and R$_3$ are as defined in formula (I). The compound of formula (Ia) is reacted with the compound of formula (IIb) R$_4$—NH$_2$, wherein R$_4$ is as above, to give compounds of formula (I), wherein R$_1$ is the group —C(R$_5$)=N—R$_4$, R$_4$ is defined as in formula 1. The reaction can be carried out with conventional methods well known to the person skilled in the art, being a normal formation of an imine. Preferably, the molar ratio between 7-aldehyde or 7-keto camptothecin and amine is comprised between 1:3 and 3:1. The salts of the amine of interest can also be used. The reaction is carried out in the presence of a base, for example an inorganic base, such as potassium carbonate, or organic, such as triethylamine or diazabicyclononene, using polar solvents, preferably methanol or ethanol and carrying out the reaction at a temperature comprised between room temperature and solvent boiling point, optionally in the presence of dehydrating agents, for example sodium or magnesium sulfate, molecular sieves. If desired it is also possible to carry out the reaction in the presence of a catalyst, for example a Lewis acid (as disclosed for example by Moretti and Torre, *Synthesis*, 1970, 141; or by Kobayashi, et al., *Synlett*, 1977, 115).

The camptothecin 7-aldehyde and the camptothecin 7-oxime are disclosed in the patent application EP 0 056 692 and in the mentioned Sawada, et al., *Chem. Pharm. Bull.*, 39, (10) 2574 (1991).

N$_1$-oxides of the compounds of formula (I) are prepared according to well-known methods of oxidation of heteroaromatic nitrogen, preferably by oxidation with acetic or trifluoroacetic acid and hydrogen peroxide, or by reaction with organic peroxyacids (A. Albini and S. Pietra, *Heterocyclic N-oxides*, CRC, 1991).

Regarding the various meanings of R$_4$, present in the different reactives of formula II, these reactives are available in the market, or can be prepared according to well-known methods in literature, which the expert in the field can resort to, completing with their own knowledge of the argument.

Pharmaceutically acceptable salts are obtained with conventional methods found in the literature, and do not necessitate of further disclosure.

The compounds disclosed in the present invention show antiproliferative activity, therefore are useful for their therapeutical activity, and posses physico-chemical properties that make them suitable to be formulated in pharmaceutical compositions.

The pharmaceutical compositions comprise at least a compound of formula (I), in an amount such as to produce a significant therapeutic effect, in particular antitumoral effect. The compositions comprised within the present invention are conventional and are obtained with commonly used methods in the pharmaceutical industry. According to the desired administration route, the compositions shall be in solid or liquid form, suitable to the oral, parenteral, intravenous route. The compositions according to the present invention comprise together with the active ingredients at least a pharmaceutically acceptable vehicle or excipient. Formulation co-adjuvants, for example solubilizing, dispersing, suspending, emulsifying agents can be particularly useful.

The compounds of formula (I) can also be used in combination with other active ingredients, for example other antitumor drugs, both in separate forms, and in a single dose form.

The compounds according to the present invention are useful as medicaments with antitumor activity, for example in lung tumors, such as the non-small cell lung tumour, tumors of the colon-rectum, prostate, gliomas.

Cytotoxic activity of the compounds of the present invention was assayed in cell systems of human tumour cells, using the antiproliferative activity test as a method of evaluation of the cytotoxic potential.

The cell line used is a lung non-small cell carcinoma that belongs to non-small cells hystotype named NCI H460.

For the in vivo studies, the solubilization was carried out in 10% DMSO in bidistilled water, being impossible the solubilization in saline, and the administration for the oral route was carried out at a volume of 10 ml/kg.

Antitumoral Activity

Atimic nu/nu Swiss mice (Charles River, Calco, Italia), ageing 10-12 weeks were used. The animals were maintained in laminar flow rooms, according to the guidelines of the United Kingdom Co-ordination Committee Cancer Research. Experimental protocols were approved by the Ethical Committee for animal experimentation of Istituto Nazionale per lo Studio e la Cura dei Tumori.

Tumour fragments of about 2×2×2 mm coming from mice to which were inoculated s.c. $10^6$ cells NCI H460/mouse, were implanted s.c. bilaterally in groups of 5 mice each.

The animals were treated with the compounds when the tumour began to be palpable. Twice a week, using a Vernier calliper, the width, minimum diameter (l), length and maximum diameter (L) of the tumors were measured, in mm. The tumour volume (mm$^3$) was calculated according to the formula $l^2 \times L/2$. Efficacy of the molecule was evaluated as TVI percent of the treated group versus the control group according to the formula TVI %=100−(T/C×100), wherein T is the mean value of the tumour volume of the treated group and C of control one. A compound is considered active when TVI %≧50.

Further advantages of these molecules can be identified in the wide interval of effective doses, indicating an increase of therapeutic index and a higher handling in the therapeutical use, in particular if a prolonged administration in the time is foreseen, above all in the injectable formulations, with the use of variable schemes and doses.

An important drawback of conventional camptothecins is the reversibility of their bond in the ternary complex (drug-DNA-enzyme). This reversibility affects drug efficacy, as it does not allow the transformation of the single strand DNA cleavage into double strand DNA cleavage during DNA synthesis.

The advantage offered by the compounds according to the present invention is evident in overcoming the limit of reversibility of the ternary complex with respect to the state of the art.

In preclinical investigations, the compounds of the present invention showed cytotoxic activity in various tumor cell lines.

This broad spectrum of anticancer activity was confirmed in mice transplanted with human tumor xenografts, including NSCLC (H460, A549), prostate ca. (JCA-1), glioblastoma (GBM/7), gastric cancer. (MKN28), osteosarcoma (U2OS), ovarian cancer (A2780/Dx, A2780/DDP) and colon (HT29, CoBA) carcinomas as well as in murine lung cancer (M109) and leukaemia model (L1210).

The preclinical data suggest that the compounds of the present invention may be an active anticancer agent against human's cancers and in particular against non-small cell lung cancer (NSCLC), glioblastoma and prostate carcinoma.

The antitumor activity of exemplary compounds of the invention is shown in the following Table 1.

TABLE 1

| Compound | IC$_{50}$ (mg/ml) | |
| --- | --- | --- |
| ST 1737 | 0.0295 ± 0.07 | (water soluble) |
| ST 2034 | 0.235 ± 0.02 | |
| ST 2069 | 0.14 ± 0.04 | |
| ST 2138 | 0.033 ± 0.004 | |
| ST 2228 | 0.036 ± 0.01 | |
| ST 2316 | 0.062 ± 0.03 | |
| ST 2317 | 0.075 ± 0.02 | |
| ST 1561 (CPT160) | 0.14 ± 0.03 | |
| ST 2412 | 0.042 ± 0.0012 | |
| ST 2212 | 0.235 ± 0.06 | |
| ST 2388 | 0.033 ± 0.004 | |
| ST 2389 | 0.015 ± 0.008 | |
| ST 2343 | 0.028 ± 0.012 | |
| ST 2477 | 0.08 ± 0.002 | |

The in vivo activity of the compound ST1737 is shown in Table 2 below.

TABLE 2

Effects of ST 1737 administered per os, q4dx4, in athymic nude mice bearing s.c. the MKN-28 human gastric carcinoma

| Drug | Dose (mg/kg) | TVI %[1] | BWL %[2] | Tox[3] |
| --- | --- | --- | --- | --- |
| ST 1737 | 4 | 69 | | 0/4 |
| | 7 | 56 | | 0/4 |
| | 12 | 68 | 4 | 0/4 |

Mean tumor doubling times in control mice were 7.1 ± 1.3 and 5.4 ± 1.4 days (exp. 656 and 664, respectively).
[1]Tumor volume inhibition % in treated over control tumors at 11–12 day after last treatment.
[2]Body weight loss % induced by drug treatment.
[3]Dead/treated mice.

The high cytotoxic potency of the compounds of the present invention, herein represented in an exemplary way with one of the preferred compounds, ST 1737, is also reflected by the potent antitumor activity. Using a panel of tumor xenografts characterized by a significant responsiveness to Topotecan (TPT) (i.e. TVI>80%), the spectrum of antitumor activity of the compounds of the present invention, against a significant number of human tumor models was substantially improved. In particular, an impressive antitumor efficacy was found in the treatment of many tumor models, where very high regressions were achieved in a large number of treated animals. Moreover, the compounds of the present invention, were able to induce substantial CR in the tumors characterized by a MDR-phenotype. This observation is of high importance, indicating that the compounds of the present invention are not a substrate for P-glycoprotein.

Additional therapeutic advantages of the compounds of the present invention are related to a) an improvement of the therapeutic index, b) drug efficacy in a large range of doses, c) evidence of efficacy using quite different schedules, making the compounds of the present invention less dependent on the treatment schedule than that of Topotecan.

The following examples further illustrate the invention.

EXAMPLE 1

General procedure: To a suspension of Yb(OTf)$_3$ (16 mg, 0.03 mmol) in 5 ml of anhydrous CH$_2$Cl$_2$ containing 4 Å MS, a solution of 7-formylcamptothecin (100 mg, 0.26 mmol) in 20 ml of CH$_2$Cl$_2$ is added, followed by a solution of the amine (0.26 mmol) in 0.5 ml of CH$_2$Cl$_2$. The resulting mixture is stirred at room temperature until the reaction is complete. After filtering the sieves, 20 ml of water are added and the two phases are separated. The aqueous layer is rapidly extracted three times with dichloromethane. The combined organic phases are dried and evaporated, and the product purified by flash chromatography on silica gel.

The following compounds were obtained. In some cases antitumor activity is shown (IC$_{50}$ on H-460, μM)

7-(2-methylphenyl)iminomethylcamptothecin (ST2212)

IC$_{50}$ (H-460, μM): 0.10 M.P. 247-248° C. dec., $^1$H NMR (DMSO-d$_6$) δ: 0.87 (t, J=7 Hz, H$_3$-18), 1.7-1.9 (m, H$_2$-19), 2.5 (s, Ar—CH$_3$), 5.4 (s, H$_2$-17), 5.60 (s, H$_2$-5), 6.55 (s, —OH), 7.25-7.50 (m, 4H Ar, H-14), 7.75 (m, H-11), 7.95 (m, H-10), 8.25 (dd, H-12), 9.10 (dd, H-9), 9.65 (s, CH═N).

7-(2-chlorophenyl)iminomethylcamptothecin (ST2228)

IC$_{50}$ (H-460, μM): 0.07 M.P. >240° C. dec., $^1$H NMR (DMSO-d$_6$) δ: 0.83 (t, J=7 Hz, H$_3$-18), 1.7-1.9 (m, H$_2$-19), 5.45 (s, H$_2$-17), 5.60 (s, H$_2$-5), 6.50 (s, —OH), 7.35-7.50 (m, H-14; 4H Arom.), 7.85 (m, H-11), 7.95 (m, H-10), 8.30 (dd, H-12), 9.10 (dd, H-9), 9.70 (s, CH═N).

7-(2,6-dimethylphenyl)iminomethylcamptothecin (ST2317)

IC$_{50}$ (H-460, μM): 0.15 M.P. 250° C. dec., $^1$H NMR (DMSO-d$_6$) δ: 0.87(t, J=7 Hz, H$_3$-18), 1.7-1.9 (m, H$_2$-19), 2.25 (s, 2Ar—CH$_3$), 5.4 (s, H$_2$-17), 5.60 (s, H$_2$-5), 6.55 (s, —OH), 7.0-7.30 (m, 3H Ar), 7.40 (s, H-14), 7.8 (m, H-11), 7.9 (m, H-10), 8.25 (dd, H-12), 8.85 (dd, H-9), 9.5 (s, CH═N).

7-(2-iodophenyl)iminomethylcamptothecin (ST2316)

IC$_{50}$ (H-460, μM): 0.06 M.P. 240° C. dec., $^1$H NMR (DMSO-d$_6$) δ: 0.87(t, J=7 Hz, H$_3$-18), 1.8-1.9 (m, H$_2$-19), 5.45 (s, H$_2$-17), 5.75 (s, H$_2$-5), 6.55 (s, —OH), 7.1-7.6 (m, 4H Ar, H-14), 7.8 (m, H-11), 7.9 (m, H-10), 8.30 (dd, H-12), 9.10 (dd, H-9), 9.65 (s, CH═N).

7-(2-methoxyphenyl)iminomethylcamptothecin (ST2343)

IC$_{50}$ (H-460, µM): 0.06 M.P. 244-246° C. dec., $^1$H NMR (DMSO-d$_6$) δ: 0.83 (t, J=7 Hz, H$_3$-18), 1.7-1.9 (m, H$_2$-19), 3.95 (s, OCH$_3$), 5.45 (s, H$_2$-17), 5.55 (s, H$_2$-5), 6.45 (s, —OH), 7.0-7.50 (m, H-14; 4H Arom.), 7.7 (m, H-11), 7.85 (m, H-10), 8.25 (dd, H-12), 8.9 (dd, H-9), 9.70 (s, CH═N).

7-(4-methylphenyl)iminomethylcamptothecin (ST2478)

IC$_{50}$ (H-460, µM): 0.18 M.P. 159-160° C. dec., $^1$H NMR (DMSO-d$_6$) δ: 0.83 (t, J=7 Hz, H$_3$-18), 1.7-1.9 (m, H$_2$-19), 2.35 (s, Ar—CH$_3$), 5.37 (s, H$_2$-17), 5.5 (s, H$_2$-5), 6.45 (s, —OH), 7.25-7.35 (m, H-14; 2H Arom.), 7.4-7.5 (m, 2H arom.), 7.7 (m, H-11), 7.85 (m, H-10), 8.16 (dd, H-12), 8.9 (dd, H-9), 9.55 (s, CH).

7-(2-hydroxyphenyl)iminomethylcamptothecin (ST2389)

IC$_{50}$ (H-460, µM): 0.06 M.P. 252-254° C. dec., $^1$H NMR (DMSO-d$_6$) δ: 0.87 (t, J=7 Hz, H$_3$-18), 1.7-1.9 (m, H$_2$-19), 5.4 (s, H$_2$-17), 5.60 (s, H$_2$-5), 6.55 (s, —OH), 6.90-7.5 (m, 4H Ar, H-14), 7.85-8.0 (m, H-11, H-10), 8.35 (dd, H-12), 8.90 (dd, H-9), 9.70 (s, CH═N).

7-(4-chlorophenyl)iminomethylcamptothecin (ST2412)

IC$_{50}$ (H-460, µM): 0.08 M.P. 246-247° C. dec., $^1$H NMR (DMSO-d$_6$) δ: 0.83 (t, J=7 Hz, H$_3$-18), 1.7-1.9 (m, H$_2$-19), 5.40 (s, H$_2$-17), 5.55 (s, H$_2$-5), 6.45 (s, —OH), 7.35 (s, H-14), 7.50-7.60 (m, 4H arom.), 7.85 (m, H-11), 7.95 (m, H-10), 8.25 (dd, H-12), 8.95 (dd, H-9), 9.55 (s, CH═N).

7-(4-methoxyphenyl)iminomethylcamptothecin (ST2477)

IC$_{50}$ (H-460, µM): 0.16 M.P. 252-255° C. dec., $^1$H NMR (DMSO-d$_6$) δ: 0.87(t, J=7 Hz, H$_3$-18), 1.7-1.9 (m, H$_2$-19), 3.8 (s, —OCH$_3$), 5.4 (s, H$_2$-17), 5.45 (s, H$_2$-5), 6.55 (s, —OH), 7.05 (d, 2H Ar), 7.35 (s, H-14), 7.60 (d, 2H Ar), 7.85 (m, H-11), 7.9 (m, H-10), 8.25 (dd, H-12), 8.8 (dd, H-9), 9.5 (s, CH).

7-[(4-isopropylidene-amino-oxymethyl)phenyl]iminomethylcamptothecin (ST2460)

IC$_{50}$ (H-460, µM): 0.01 M.P. 147° C. dec., $^1$H NMR (DMSO-d$_6$) δ: 0.85 (t, J=7 Hz, H$_3$-18), 1.7-1.9 (m, H$_2$-19, C(CH$_3$),2), 5.05 (s, CH$_2$—O), 5.40-5.55 (m, H$_2$-17, H$_2$-5), 6.50 (s, —OH), 7.35 (s, H-14), 7.40-7.60 (m, 4H arom.), 7.75-7.85 (m, H-11), 7.86-7.95 (m, H-10), 8.25 (dd, H-12), 8.95 (dd, H-9), 9.60 (s, CH═N).

7-(2-t-butylphenyl)iminomethylcamptothecin (ST2388)

IC$_{50}$ (H-460, µM): 0.07 M.P. 215° C. dec., $^1$H NMR (DMSO-d$_6$) δ: 0.85 (t, J=7 Hz, H$_3$-18), 1.45 (s, 9H, tBut), 1.7-1.9 (m, H$_2$-19), 5.35-5.75 (m, H$_2$-17, H$_2$-5), 6.50 (s, —OH), 7.05-7.5 (m, H-14; 4H arom.), 7.75-7.85 (m, H-11), 7.88-7.95 (m, H-10), 8.25 (dd, H-12), 8.95 (dd, H-9), 9.45 (s, CH═N).

7-phenyliminomethylcamptothecin (ST1546)

IC05 (H-460, µM): 0.13 $^1$H NMR (DMSO-d$_6$) δ: 0.83 (t, J=7 Hz, H$_3$-18), 1.7-1.9 (m, H$_2$-19), 5.37 (s, H$_2$-17), 5.5 (s, H$_2$-5), 6.45 (s, —OH), 7.25-7.35 (m, H-14; H arom.), 7.4-7.5 (m, 4H arom), 7.7 (m, H-11), 7.85 (m, H-10), 8.16 (dd, H-12), 8.9 (dd, H-9), 9.55 (s, CH═N)

7-(4-nitrophenyl)iminomethylcamptothecin (ST1561)

IC$_{50}$ (H-460, µM): 0.28 M.P. 260-265° C. dec. $^1$H NMR (DMSO-d$_6$) δ: 0.85 (t, J=7 Hz, H$_3$-18), 1.7-1.9 (m, H$_2$-19), 5.35 (s, H$_2$-17), 5.48 (s, H$_2$-5), 6.45 (s, —OH), 7.3 (s, H-14), 7.6-7.7 (m, 2 Ar), 7.8 (m, H-11), 7.9 (m, H-10), 8.25 (dd, H-12), 8.35-8.40 (m, 2 Ar), 8.9 (dd, H-9), 9.67 (s, CH═N).

7-2-(2-aminophenyldithio)phenyliminomethylcamptothecin (ST1737)

IC$_{50}$ (H-460, µM): 0.017 $^1$H NMR (DMSO-d$_6$) δ: 0.83 (t, J=7 Hz, H$_3$-18) 1.7-1.9 (m, H$_2$-19) 5.35 5.75 (6H, m, H$_2$-5+H-17+NH$_2$), 6.40 (1H, m, ArH), 6.5-6.6 (2H, m, 1 ArH+OH), 6.90 (1H, m, ArH), 7.25-7.45 (4H, m, 3 ArH+H-14), 7.15-8.0 (4H, m, 4 ArH), 8.25 (1H, dd), 9.75 (1H, s, CH═N).

7-4-(4-aminophenyldithio)phenyliminomethylcamptothecin (ST2034)

IC$_{50}$ (H-460, µM): 0.39 M.P. 154-155° C. dec., $^1$H NMR (DMSO-d$_6$) δ: 0.83 (t, J=7 Hz, H$_3$-18), 1.7-1.9 (m, H$_2$-19), 5.40 (s, H$_2$-17), 5.55 (s, H$_2$-5+NH$_2$), 6.50 (s, —OH), 6.55 (m, 2H Ar), 7.25 (m, 2H Ar), 7.35 (s, H-14), 7.60 (m, 4H Ar), 7.8 (m, H-11), 7.9 (m, H-10), 8.25 (dd, H-12), 9.0 (dd, H-9), 9.70 (s, CH═N).

7-4-(4-aminophenylthio)phenyliminomethylcamptothecin (ST2069)

IC$_{50}$ (H-460, µM): 0.24 M.P. 187-188° C. dec., $^1$H NMR (DMSO-d$_6$) δ: 0.87 (t, J=7 Hz, H$_3$-18), 1.7-1.9 (m, H$_2$-19), 5.4 (s, H$_2$-17), 5.55 (s, H$_2$-5+NH$_2$), 6.55 (s, —OH), 6.65 (m, 2H Ar), 7.10-7.50 (m, 6H Ar+H-14), 7.8 (m, H-11), 7.9 (m, H-10), 8.30 (dd, H-12), 9.0 (dd, H-9), 9.5 (s, CH═N).

7-(2-methylthiophenyl)iminomethylcamptothecin (ST2138)

IC$_{50}$ (H-460, µM: 0.06 M.P. >250° C. dec., $^1$H NMR (DMSO-d$_6$) δ: 0.83 (t, J=7 Hz, H$_3$-18), 1.7-1.9 (m, H$_2$-19), 2.50 (s, SCH$_3$), 5.40 (s, H$_2$-17), 5.70 (s, H$_2$-5), 6.45 (s, —OH), 7.25-7.35 (m, H-14; 3H arom.), 7.6 (m, 1H arom), 7.8 (m, H-11), 7.95 (m, H-10), 8.30 (dd, H-12), 9.10 (dd, H-9), 9.55 (s, CH═N).

EXAMPLE 2

To a suspension of 20S-camptothecin-7-aldehyde (1) (100 mg, 0.26 mmol) in 7 mL anhydrous CH$_2$Cl$_2$, the appropriate amine (0.78 mmol) and Yb(OTf)3 (16 mg, 0.03 mmol) were added. The resulting mixture was stirred at room temperature until the reaction was complete. After filtering the sieves the solvent was evaporated, and the product purified by flash chromatography on silica gel (Merck 230-400 mesh).

The following compounds were obtained

7-(4-tert-butylphenyliminomethyl)-camptothecin (ST 2619)

The solution is stirred 1.5 h. Flash chromatography (eluent: $CH_2Cl_2$:MeOH 99:1). Yellow powder. Yield 50%, M.P. 250° C. dec., $^1$H NMR (DMSO-$d_6$) δ: 0.88 (t, J=7 Hz, H3-18), 1.30 (s, tBut), 1.75-1.95 (m, H2-19), 5.45 (s, H2-17), 5.55 (s, H2-5), 6.55 (s, —OH), 7.35 (s, H-14), 7.45-7.60 (m, 41H Ar), 7.80 (m, H-11), 7.95 (m, H-10), 8.25 (dd, H-12), 8.95 (dd, H-9), 9.7 (s, CH=N). $IC_{50}$ (H-460, μM): 0.09

7-(4-methylthiophenyliminomethyl)-camptothecin (ST 2667)

The solution is stirred 22 h. Flash chromatography (eluent: $CH_2Cl_2$:MeOH 98:2). Yellow powder. Yield 36%, M.P. 160° C. dec., $^1$H NMR (DMSO-d6) δ: 0.87 (t, J=7 Hz, H3-18), 1.7-1.9 (m, H2-19), 2.55 (s, —$SCH_3$), 5.45 (s, H2-17), 5.55 (s, H2-5), 6.50 (s, —OH), 7.35 (s, H-14), 7.40 (d, 2H Ar), 7.55 (d, 2H Ar), 7.80 (m, H-11), 7.9 (m, H-10), 8.20 (dd, H-12), 8.95 (dd, H-9), 9.7 (s, CH=N). $IC_{50}$ (H-460, μM): 0.074

7-(4-hydroxyphenyliminomethyl)-camptothecin (ST 2616)

The solution is stirred 3 h. Flash chromatography (eluent: $CH_2Cl_2$:MeOH 96:4). Yellow powder. Yield 79%, M.P. 250° C. dec., $^1$H NMR (DMSO-$d_6$) δ: 0.90 (t, J=7 Hz, H3-18), 1.75-2.0 (m, H2-19), 5.4 (s, H2-17), 5.55 (s, H2-5), 6.50 (s, —OH), 6.90 (d, 2H Ar), 7.35 (s, H-14), 7.55 (d, 2H Ar), 7.80 (m, H-11), 7.90 (m, H-10), 8.25 (dd, H-12), 9.0 (dd, H-9), 9.70 (s, CH=N). $IC_{50}$ (H-460, μM): 0.22

The invention claimed is:

1. A method for treating a subject suffering from a tumor selected from the group consisting of non-small cell lung tumor and gastric cancer comprising administering to said subject a compound of formula (I)

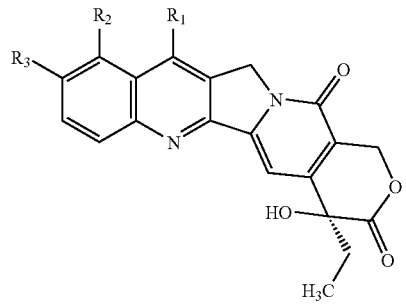

wherein: $R_1$ is a —$C(R_5)$=N—$R_4$ group, wherein $R_4$ is a phenyl group substituted with one or more keto groups; —S—S-(2-aminophenyl), —S—S-(4-aminophenyl), —S-(4-aminophenyl), —$SCH_3$ and —$CH_2ON$=$C(CH_3)_2$;

$R_5$ is hydrogen, $C_1$-$C_8$ linear or branched alkyl, $C_1$-$C_8$ linear or branched alkenyl, $C_3$-$C_{10}$ cycloalkyl, ($C_3$-$C_{10}$) cycloalkyl-($C_1$-$C_8$) linear or branched alkyl, $C_6$-$C_{14}$ aryl, ($C_6$-$C_{14}$) aryl-($C_1$-$C_8$) linear or branched alkyl;

$R_2$ and $R_3$, the same or different between them are hydrogen, hydroxy, $C_1$-$C_8$ linear or branched alkoxy;

their $N_1$-oxides, their single isomers, in particular the syn and anti isomers of the —$C(R_5)$=N—$R_4$ group, their possible enantiomers, diastereoisomers and relative admixtures, and the pharmaceutically acceptable salts thereof.

2. The method according to claim 1 wherein the phenyl group is substituted in the ortho-position.

3. A method for treating a subject suffering from a tumor selected from the group consisting of non-small cell lung tumor and gastric cancer comprising administering to said subject a compound selected from the group consisting of:

7-2-(2-aminophenyldithio)phenyliminomethylcamptothecin (ST1737)

7-4-(4-aminophenyldithio)phenyliminomethylcamptothecin (ST2034)

7-4-(4-aminophenylthio)phenyliminomethylcamptothecin (ST2069)

7-(2-methyhhiophenyl)iminomethylcamptothecin (ST2138)

their $N_1$-oxides, their single isomers, in particular the syn and anti isomers of the —$C(R_5)$=N—$R_4$ group, their possible enantiomers, diastereoisomers and relative admixtures, and the pharmaceutically acceptable salts thereof.

* * * * *